US00RE48818E

(19) United States
(12) Reissued Patent
Bach et al.

(10) Patent Number: US RE48,818 E
(45) Date of Reissued Patent: Nov. 16, 2021

(54) HOT-MELT ADHESIVE SUBSTANCE

(71) Applicant: Clariant Plastics & Coatings Ltd, Muttenz (CH)

(72) Inventors: Sebastian Bach, Langweid (DE); Gerd Hohner, Gersthofen (DE)

(73) Assignee: Clariant International Ltd, Muttenz (CH)

(21) Appl. No.: 16/237,506

(22) Filed: Dec. 31, 2018

Related U.S. Patent Documents

Reissue of:
(64) Patent No.: 8,487,026
Issued: Jul. 16, 2013
Appl. No.: 12/445,913
PCT Filed: Oct. 6, 2007
PCT No.: PCT/EP2007/008691
§ 371 (c)(1),
(2) Date: Apr. 16, 2009
PCT Pub. No.: WO2008/046536
PCT Pub. Date: Apr. 24, 2008

(30) Foreign Application Priority Data

Oct. 18, 2006 (DE) ..... 102006049089

(51) Int. Cl.
*C09J 123/08* (2006.01)
*A61L 15/58* (2006.01)
*B32B 7/12* (2006.01)
*C09J 123/10* (2006.01)
*C08L 23/22* (2006.01)

(52) U.S. Cl.
CPC ..... *C09J 123/0815* (2013.01); *A61L 15/58* (2013.01); *B32B 7/12* (2013.01); *C09J 123/10* (2013.01); *C08L 23/22* (2013.01); *C08L 2666/02* (2013.01)

(58) Field of Classification Search
CPC .... C09J 123/14; C09J 123/08; C08G 2170/20
See application file for complete search history.

(56) References Cited

U.S. PATENT DOCUMENTS 4,962,262 A 10/1990 Winter et al.
5,023,388 A 6/1991 Luker
5,081,322 A 1/1992 Winter et al. ..... C08F 210/06 585/9
5,346,732 A 9/1994 Lai et al.
5,639,327 A * 6/1997 Mody et al. ..... 156/148
5,723,705 A 3/1998 Herrmann et al.
5,750,813 A 5/1998 Hess et al.
5,763,516 A * 6/1998 Godfrey ..... 524/271
5,998,547 A 12/1999 Hohner
6,120,887 A 9/2000 Werenicz et al.
6,143,846 A 11/2000 Herrmann et al.
6,331,590 B1 12/2001 Herrmann et al.
6,664,309 B2 12/2003 Svenningsen et al.
6,747,114 B2 * 6/2004 Karandinos et al. ..... 526/348.2
6,797,774 B2 9/2004 Kijima
7,825,186 B2 11/2010 Bach et al.
8,129,464 B2 3/2012 Abba et al.
8,487,026 B2 7/2013 Bach et al.
2002/0115744 A1 8/2002 Svenningsen
2004/0052952 A1 3/2004 Vey et al.
2004/0054343 A1 3/2004 Barnett et al.
2004/0127614 A1 * 7/2004 Jiang ..... C09J 123/12 524/270
2005/0054779 A1 3/2005 Zhou
2005/0159566 A1 7/2005 Minami et al.
2005/0288412 A1 * 12/2005 Hohner ..... C09J 123/14 524/384
2006/0074171 A1 4/2006 Bach et al.
2006/0199897 A1 9/2006 Karjala et al.
2006/0222815 A1 10/2006 Oles
2006/0235134 A1 10/2006 Bach et al.
(Continued)

FOREIGN PATENT DOCUMENTS

DE 196 48 895 A1 5/1998
DE 19648895 5/1998
(Continued)

OTHER PUBLICATIONS

Clariant submission to the European Patent Office on Jul. 17, 2017 (Year: 2017).*
Dow Chemical Co., "Affininty GA Polyolefin Plastomers—Plastics—Asia Pacific," dated Mar. 2005, 8 pages.
ExxonMobil Chemical Datasheet, "Escorez 5320 Tackifying Resin," dated Dec. 5, 2012, 1 page.
EPO Registry, European Patent No. 2081609, Bostik Inc., "Analytical Test Report—A sample of Affinity GA-1900 and GA-1950 were submitted for evaluation," dated Dec. 20, 2012.
ASTM International, "Designation: D 3104-99—Standard Test Method for Softening Point of Pitches (Mettler Softening Point Method)," dated Mar. 2000, 6 pages.
ASTM International, "Designation: E 28-99—Standard Test Methods for Softening Point of Resins Derived from Naval Stores by Ring-and-Ball Apparatus," dated Feb. 2000, 6 pages.
(Continued)

*Primary Examiner* — Timothy J. Kugel
(74) *Attorney, Agent, or Firm* — McDonnell Boehnen Hulbert & Berghoff LLP

(57) ABSTRACT

The invention relates to a hot-melt adhesive substance for sticking together fibrous materials such as matted nonwovens or woven textiles with smooth substrate surfaces, such as plastic or metal films, and for laminating said materials. Said substance is characterized in that it contains at least one polyolefin which has been produced by polymerization in the presence of metallocene as a catalyst and has a ring/ball softening point of between 50 and 165° C. and a melting viscosity, measured at a temperature of 170° C., of between 20 and 40,000 mPa-s. The hot-melt adhesive substance can also contain at least one adhesive component and is used in a quantity of between 3 and 6 g/m$^2$, preferably between 4 and 5.5 g/m$^2$, for sticking a film to a nonwoven material during the production of hygiene items such as disposable nappies, baby nappies, incontinence products, panty liners and/or sanitary towels.

91 Claims, No Drawings

(56) References Cited

U.S. PATENT DOCUMENTS

| | | | |
|---|---|---|---|
| 2007/0117894 | A1 | 5/2007 | Bach et al. |
| 2007/0117906 | A1 | 5/2007 | Bach et al. |
| 2007/0117907 | A1 | 5/2007 | Bach et al. |
| 2008/0262148 | A1 | 10/2008 | Bach et al. |

FOREIGN PATENT DOCUMENTS

| | | | |
|---|---|---|---|
| DE | 10 2004 048 536 | A1 | 12/2004 |
| DE | 103 23 617 | A1 | 12/2004 |
| DE | 10323617 | | 12/2004 |
| DE | 102004048536 | | 4/2006 |
| EP | 0 321 851 | A1 | 12/1988 |
| EP | 0 321 852 | A1 | 12/1988 |
| EP | 0321851 | | 6/1989 |
| EP | 0321852 | | 6/1989 |
| EP | 0 384 264 | A1 | 2/1990 |
| EP | 0384264 | | 8/1990 |
| EP | 0 571 882 | A2 | 5/1993 |
| EP | 0571882 | | 12/1993 |
| EP | 0 890 584 | A1 | 7/1998 |
| EP | 0890584 | | 1/1999 |
| EP | 1 295 925 | A1 | 3/2003 |
| EP | 1 375 731 | A1 | 1/2004 |
| EP | 1 645 608 | A1 | 9/2005 |
| EP | 1645608 | | 4/2006 |
| EP | 1 788 054 | A1 | 11/2006 |
| EP | 1 788 055 | A1 | 11/2006 |
| EP | 1 788 056 | A1 | 11/2006 |
| WO | 97/33921 | | 9/1997 |
| WO | WO 97/33921 | A1 | 9/1997 |
| WO | WO 98/23652 | * | 6/1998 |
| WO | WO 98/23652 | A1 | 6/1998 |
| WO | WO 01/14487 | | 3/2001 |
| WO | WO 01/14487 | A1 | 3/2001 |
| WO | WO 02/45763 | | 6/2002 |
| WO | WO 02/45763 | A2 | 6/2002 |
| WO | WO 2004/104128 | | 12/2004 |
| WO | WO 2004/104128 | A1 | 12/2004 |
| WO | WO 2006/004750 | A1 | 1/2006 |
| WO | 2007/047232 | A1 | 4/2007 |

OTHER PUBLICATIONS

Clariant Int'l Ltd, "Licocene(R) Grades—The 'Designer Polymers'," Aug. 2007, 2 pages.
Dow Chemical Co., Fact Sheet, "Affinity GA Polyolefin Plastomers—A line of highly versatile polymers developed for hot-melt adhesive formulations and a range of polymer modification applications," dated Oct. 10, 2006,2 pages.
Dow Chemical Co., "Affinity GA Polyolefin Plastomers—Plastics-Global," dated Aug. 2004, 8 pages.
DIN 53019-1, "Viscometry—Measurement of viscosities and flow curves by means of rotational viscometers—Part 1: Principles and geometry of measuring system. English translation of DIN 53019-1:2009-09," Sep. 2008, 22 pages.
DIN 53019-2," Viscometry—Determiantion of viscosity and flow curves with rotational viscometers. Part 2: Viscometer calibration and determination of uncertainty of measurement," dated Feb. 2001, 25 pages.
DIN 53019-3, "Viscometry—Measurement of viscosities and flow curves by means of rotational viscometers. Part 3: Measurement errors and corrections. English translation of DIN 53019-3:2008-09," dated Sep. 2008, 22 pages.
Dow Chemical Co., "Hot Melt Adhesives—Plastics-Global. Getting a Grip with Better Hot Melts," Published Aug. 2004, 8 pages.
EPO Registry, European Patent No. 2081609, Declaration of Selim Yalvac Concerning Opposition by Dow to EP 2 081 609 B1, dated Apr. 24, 2015, 3 pages.
EPO Registry, European Patent No. 2081609, Declaration of Selim Yalvac Re: EP-B1-2 081 609, dated Apr. 24, 2015, 2 pages.
Dow Chemical Co., Technical Information, "Affinity GA 1900 Polyolefin Plastomer," Rev: 2011-08-29,2 pages.
Dow Chemical Co., Technical Information, "Affinity GA 1950 Polyolefin Plastomer," Rev: 2011-08-29,2 pages.
ASTM International, "Designation: E 1356-03. Standard Test Method for Assignment of the Glass Transition Temperatures by Differential Scanning Calorimetry," dated May 2003, 4 pages.
EPO Registry, European Patent No. 2081609, Patent Owner citation D3, Bestimmung der Schmelzviskositat und des Erweichungspunkts fur drei erfindungsgemasse Polymere, dated May 15, 2015, 2 pages, provided with English Translation.
EPO Registry, European Patent No. 2081609, Declaration of Dr. Gerd Hohner, dated May 15, 2015, 4 pages, provided with English Translation.
Othman, D et al., "A Comparison of On-Site and Elevated Temperature Cure of an FRP Strengthening Adhesive," Edinburgh Research Explorer, the University of Edinburgh, (2013) 11 pages.
EPO Registry, European Patent No. 2081609, Patent Owner citation D2, Verhaltnis von Schmelzflussindex und viskositat, dated May 15, 2015, 1 page, provided with English translation.
EPO Registry, European Patent No. 2081609, Patent Owner citation D3, Vlies-spezifische Anwendung der Heissschmelzklebemassen, dated Dec. 21, 2015, 3 pages, provided with English translation.
International Search Report issued in International Patent Application No. PCT/EP/2007/008366, dated Jan. 2, 2008, 3 pages, provided with English Translation.
Clariant GmbH, "Licocene(R) Grades—the 'Designer Waxes'," dated Nov. 2003, 2 pages.
Sebastijn Bach, "Licocene(R) Performance Polymers as SIS Replacement," dated Oct. 2005, 38 pages.
EPO Registry, European Patent No. 2081609, marked up version of U.S. Pat. No. 6,797,774, filed Jul. 14, 2016.
EPO Registry, European Patent No. 2081609, Notice of Opposition, H.B. Fuller Co., dated Dec. 19, 2012.
EPO Registry, European Patent No. 2081609, Notice of Opposition, Bostik Inc., dated Dec. 21, 2012.
EPO Registry, European Patent No. 2081609, Notice of Opposition, The Dow Chemical Co., dated Dec. 21, 2012.
EPO Registry, European Patent No. 2081609, Patent Owner Response, dated Aug. 16, 2013, provided with English translation.
EPO Registry, European Patent No. 2081609, Patent Owner letter with requests for claim amendments, dated Dec. 10, 2013, provided with English translation.
EPO Registry, European Patent No. 2081609, H.B. Fuller letter regarding claim amendments, dated Jul. 15, 2014.
EPO Registry, European Patent No. 2081609, Opposition Division communication in advance of Oral Proceedings, dated Dec. 3, 2014, provided with English translation.
EPO Registry, European Patent No. 2081609, Dow letter in advance of Oral Proceedings, dated Apr. 28, 2015.
EPO Registry, European Patent No. 2081609, Dow letter in advance of Oral Proceedings, dated May 13, 2015.
EPO Registry, European Patent No. 2081609, Patent Owner letter in advance of Oral Proceedings with main and auxiliary requests for claim amendments, dated May 15, 2015, provided with English translation.
FPO Registry, European Patent No. 2081609, Fuller Response to Statement of Grounds of Appeal, dated May 12, 2016.
FPO Registry, European Patent No. 2081609, Dow Response to Statement of Grounds of Appeal, dated Jul. 12, 2016.
EPO Registry, European Patent No. 2081609, Patent Owner letter regarding Appeal Procedure, dated Nov. 15, 2016, provided with English translation.
EPO Registry, European Patent No. 2081609, Third Party Observations, dated May 4, 2017, provided with English translation.
EPO Registry, European Patent No. 2081609, Dow letter regarding Patent Owner Response to Third Party Observations, dated Dec. 4, 2017.
Clariant GmbH, "Licocene(R) Grades—The 'Designer Polymers'," dated Aug. 2007, 2 pages.
PCT International Search Report, PCT/EP2007/008691, dated Jan. 17, 2008.
English Translation of International Preliminary Report on Patentability, PCT/EP2008/08691, dated Jun. 18, 2009.
Declaration of Peijun Jiang, Ph.D. Date: Jul. 24, 2019.

(56) References Cited

OTHER PUBLICATIONS

Declaration of Jean-Roch Schauder, Ph.D. Date: Jul. 25, 2019.
Publication: A new decoupling method for accurate quantification of polyethylene copolymer composition and triad sequence distribution with 13C NMR, Journal of Magnetic Resonance 187 (2007) 225-233 Authors: Zhe Zhou, Rainer Kümmerle, Xiaohua Qiu, David Redwine, Rongjuan Cong, Angela Taha, Dan Baugh, Bill Winniford Publication Date: May 23, 2007.
Publication: Alk-1-ene Polymerization in the Presence of a Monocyclopentadienyl Zirconium(IV) Acetamidinate Catalyst: Microstructural and Mechanistic Insights, Macromolecular Rapid Communications 28 (2007) 1128-1134 Authors: Vincenzo Busico, Philippe Carbonniere, Roberta Cipullo, Roberta Pellecchia, John R. Severn, Giovanni Talarico Publication Date: 2007.
Publication: A Review of High Resolution Liquid 13Carbon Nuclear Magnetic Resonance Characterizations of Ethylene-Based Polymers, Journal of Macromolecular Science—Reviews in Macromolecular Chemistry and Physics, C29(2 & 3), 201-317(1989) Authors: James C. Randall Publication Date: 1989.
Submission of Clariant International Ltd. to European Patent Office re: EP 2081609 Date: Jul. 17, 2017 Certificate of Accuracy of Exhibit B-1a.
Clariant presentation titled "Licocene® Performance Polymers as SIS Replacement" Date: Oct. 2005.
Publication: On the viscosity-temperature behavior of polymer melts, Rheologica Acta, vol. 34, Issue 5, pp. 496-503 Authors: Jeou-shyong Wang, Roger S. Porter Publication Date: Sep. 1995 Pages Submitted: All.
Material Safety Data Sheet for Resin 835 A Date: Nov. 15, 2013.
Publication: DIN 53019-1, Viscometry—Measurement of viscosities and flow curves by means of rotational viscometers—Part 1: Principles and geometry of measuring system, English translation of DIN 53019-1:2008-09 Publication Date: Sep. 2008 Pages Submitted: All.
Website: https://www.astm.org/Standards/D3104.htm Last Visited: Jul. 22, 2019.
Website: https://en.wikipedia.org/wiki/Textile Last Visited: Jul. 22, 2019.
Website: https://www.en-standard.eu/din-en-1427-bitumen-and-bituminous-binders-determination-of-the-softening-point-ring-and-ball-method/ Last Visited: Jul. 22, 2019.
Website: https://www.astm.org/Standards/E1356.htm Last Visited: Jul. 22, 2019.
Website: https://en.wikipedia.org/wiki/Paper Last Visited: Jul. 22, 2019.
Website: https://en.wikipedia.org/wiki/Melt_flow_index Last Visited: Jul. 22, 2019.
Website: https://en.wikipedia.org/wiki/Polyethylene_terephthalate Last Visited: Jul. 22, 2019.
Website: https://www.merriam-webster.com/dictionary/film Last Visited: Jul. 22, 2019.
Website: https://en.wikipedia.org/wiki/Polyester Last Visited: Jul. 22, 2019.
Website: https://en.wikipedia.org/wiki/Tackifier Last Visited: Jul. 22, 2019.
Website: https://en.wikipedia.org/wiki/Glass_transition Last Visited: Jul. 22, 2019.
Website: https://en.wikipedia.org/wiki/Benzene Last Visited: Jul. 22, 2019.
Website: https://www.astm.org/Standards/E794.htm Last Visited: Jul. 24, 2019.
Claim chart for Jiang.
Claim chart for Hohner.
Claim chart for Bach '186.
Claim chart for Bach '134.
ASTM International, "Designation: D3104-99 (Reapproved 2010)—Standard Test Method for Softening Point of Pitches (Mettler Softening Point Method)," Dated May 2010, 6 pages.
EPO Registry, EP Pat. No. 2081609, Mailwald letter in advance of oral proceedings, May 15, 2015.
EPO Registry, EP Pat. No 2081609, Decision on Opposition with Grounds and Annex, Aug. 10, 2015, provided with English translation.
EPO Registry, EP Pat. No. 2081609, Appeal Against Decision on Opposition, Dec. 18, 2015, provided with English translation.
EPO Registry, EP Pat. No. 2081609, Bandplay Response to Statement of Grounds of Appeal, Jul. 14, 2016.
EPO Registry, EP Pat. No. 2081609, Patent Owner Response to 3rd Party Observations, Jul. 17, 2017, with requests for amended claims and document list, provided with English translation.
EPO Registry, EP Pat. No. 2081609, Maiwald letter re: Appeal, Dec. 29, 2017.I.
Clariant, Licocene(R) p. 6102 Granules, Sep. 13, 2017.
EPO Registry, EP Pat. No. 2081609, Farago letter re: Appeal, Nov. 13, 2019, provided with English translation.
EPO Registry, EP Pat. No 2081609, EPO Communication re: Appeal, Dec. 20, 2019, provided with English translation.
EPO Registry, EP Pat. No. 2081609, V.O. letter re: Appeal, Feb. 21, 2020.
EPO Registry, EP Pat. No. 2081609, Farago letter re: Appeal, Feb. 28, 2020, provided with English translation.
EPO Registry, EP Pat. No. 2081609, Bandplay letter re: Appeal, Feb. 28, 2020.
EPO Registry, EP Pat. No. 2081609, Farago letter re: Appeal, Mar. 9, 2020, provided with English translation.
EPO Registry, EP Pat. No. 2081609, Bandplay letter re: Appeal, Jan. 22, 2021.
PCT International Search Report for PCT/EP2007/008691, mailed Jan. 17, 2008.
English Translation of International Preliminary on Patentability for PCT/EP2007/008691mailed Jun. 18, 2009.

* cited by examiner

HOT-MELT ADHESIVE SUBSTANCE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This application is a reissue of U.S. Pat. No. 8,487,026, which issued on Jul. 16, 2013.*

The invention relates to a hot melt adhesive for adhesively bonding fibrous materials such as random fiber nonwovens or woven textiles to smooth substrate surfaces such as plastic films or metal foils.

Numerous hygiene articles, in particular panty diapers and panty liners but also special wipes for cleaning and disinfection are made up, depending on their intended uses, of different, multilayer materials. Thus, panty diapers comprise an inner layer which is readily permeable to liquids, then a fibrous inner layer, preferably a nonwoven, which contains absorbent materials such as superabsorbents and finally an outer plastic film which is impermeable to water and liquids of all types. The multilayer materials have to be joined to one another sufficiently strongly for them not to delaminate or slip during their intended use and also for them to offer sufficiently good comfort when worn. Since, during use, the hygiene articles concerned are mostly in direct contact with body parts where the wearer is particularly sensitive to external irritation, they must not have any rigid or sharp holding elements which can theoretically lead to skin injuries. Furthermore, there must also be no unyielding, hard join which exerts pressure on the skin or generates friction.

These circumstances mean that the adhesives, in particular the adhesives for adhesively bonding the surface of the nonwoven to the water-impermeable film have to meet demanding requirements. Thus, the adhesive bond has to be very strong and durable even at elevated temperatures, it has to withstand considerable mechanical stresses and it must not be water-sensitive. The elasticity and flexibility of the various materials in the hygiene article and also their use properties must not be impaired by the presence of the adhesive. For toxicological and ecotoxicological reasons, solvent-free adhesives which can be applied or sprayed on in very thin layers and have a high adhesive strength even in very small amounts by weight are required. The manufacture of particularly light articles having good comfort when worn should be made possible in this way.

Hot melt adhesives containing styrene-isoprene-containing or styrene-butadiene-containing block copolymers, for example hydrogenated styrene-butadiene block copolymers obtainable under the trade name KRATON, are prior art. Styrene block copolymers as such without additional tackifiers are not sticky (do not have tack). To achieve tack and a plasticity required for the application, resins or oils are added to the styrene-containing block copolymers. These additives are permanently sticky and difficult for the user to handle. In addition, they tend to penetrate through the nonwoven, which can lead to colored spots and a less favorable optical appearance of the hygiene articles. Furthermore, relatively thick nonwoven materials are necessary when such hot melt adhesives are used, which runs counter to the consumers' desire for thin and light hygiene articles.

WO 01/14487 describes hot melt adhesives and their use as construction adhesives in the production of diapers. The hot melt adhesives contain copolymers of ethylene and $C_3$-$C_{20}$-alpha-olefins prepared in the presence of metallocene as catalyst, in particular ethylene-1-butene copolymers as are obtainable, for instance, under the trade name EXACT or ethylene-1-octene copolymers as are obtainable under the trade names AFFINITY and ENGAGE. However, the adhesive strengths of the adhesives described there are capable of improvement.

DE 102 004 048536 and DE 103 23 617 describe hot melt adhesives containing polyolefin waxes prepared using metallocene compounds as catalysts and their use. These references also disclose that such polyolefin waxes have glass transition temperatures $T_g$ of less than or equal to −10° C. It was therefore an object of the present invention to develop a hot melt adhesive which is solvent-free, odorless and both toxicologically and ecotoxicologically acceptable. The hot melt adhesive sought should have a viscosity of less than 15 000 mPa·s at a temperature of 150° C. and be able to be sprayed and applied uniformly as a very thin film at temperatures in the range from 100 to 180° C., without penetrating completely through the nonwoven material. Furthermore, a hot melt adhesive which displays its full adhesive effect and develops a very good adhesive strength even at a weight per unit area of less than 6 g/m$^2$ is desired.

This object is achieved by a hot melt adhesive of the type mentioned at the outset, whose characterizing feature is that it contains at least one polyolefin which has been prepared by polymerization in the presence of metallocene as catalyst and has a ring/ball softening point in the range from 50 to 165° C. and a melt viscosity measured at a temperature of 170° C. in the range from 20 to 40 000 mPa·s.

It has surprisingly been found that the hot melt adhesive of the invention is particularly suitable as hot melt adhesive for adhesively bonding fiber materials such as nonwoven material to films and for laminating hygiene articles when it contains one or more polyolefin(s) having a glass transition temperature $T_g$ of not more than −10° C. and a melt flow index MFI of greater than 30 g/10 min, measured in accordance with ISO 1133 at a temperature of 190° C. and under a load of 2.16 kg.

Furthermore, it has been found that the hot melt adhesive of the invention can also be used advantageously for the adhesive bonding of textile materials, e.g. woven fabrics.

The hot melt adhesive of the invention has outstanding properties in respect of its adhesive strength to the respective substrates even at temperatures in the range from 37 to 50° C. and it can, especially at viscosities in the range from 200 to 10 000 mPa·s at 150° C., be sprayed in a very thin layer onto surfaces. It surprisingly shows no tendency to penetrate through fibrous material such as nonwoven material or textile layers. The hot melt adhesive of the invention is not permanently sticky but becomes sticky only on processing from the melt and is therefore easy to handle for a user in the manufacture of hygiene articles of all types.

The hot melt adhesive of the invention has good internal elasticity which is retained even at low temperatures and easily withstands the repeated deformations of the nonwoven and film materials adhesively bonded by means of it. It is water-insoluble, so that undesirable detachment phenomena cannot occur in the presence of water or high atmospheric humidity.

Another advantage is the comparatively low viscosity at 100-180° C. of the hot melt adhesive of the invention, which makes particularly low processing temperatures possible.

Shrinkage effects which can easily occur every now and again at high processing temperatures are thus avoided.

The hot melt adhesive of the invention preferably contains polyolefin(s) having melt viscosities measured at a temperature of 170° C. of from 50 to 30 000 mPa·s, particularly preferably from 100 to 20 000 mPa·s.

The hot melt adhesive of the invention is water- and solvent-free and also does not contain any [plasticators and/or] plasticizers.

Preference is also given to a hot melt adhesive containing the abovementioned polyolefins when these have a number average molar mass $M_n$ in the range from 500 to 20 000 g/mol, preferably from 800 to 10 000 g/mol, particularly preferably from 1000 to 5000 g/mol, and a weight average molar mass $M_w$ in the range from 1000 to 40 000 g/mol, preferably from 1600 to 30 000 g/mol and particularly preferably from 2000 to 20 000 g/mol. The molar mass is determined by gel permeation chromatography.

In a likewise preferred embodiment of the invention, the polyolefins present in the hot melt adhesive of the invention are homopolymers of propylene or higher 1-olefins or copolymers of olefins comprising propylene and/or higher 1-olefins and also, if appropriate, ethylene. As higher 1-olefins, preference is given to using linear or branched olefins having from 4 to 20 carbon atoms, preferably from 4 to 6 carbon atoms. These olefins can have an aromatic substituent conjugated with the olefinic double bond. Examples of possible 1-olefins are 1-butene, 1-hexene, 1-octene and 1-octadecene and also styrene. The copolymers preferably comprise from 70 to 99.9% by weight, particularly preferably from 80 to 99% by weight, of one type of olefin. Two or more of the olefins mentioned can be used for preparing the copolymers.

In a further preferred embodiment of the invention, the polyolefin present in the hot melt adhesive of the invention is a copolymer of propylene with at least one or more further monomers selected from among ethylene and linear or branched 1-olefins having from 4 to 20 carbon atoms, preferably from 4 to 10 carbon atoms, with the content of structural units derived from propylene preferably being from 70 to 99.9% by weight, particularly preferably from 80 to 99% by weight.

In a further embodiment, the polyolefin present in the hot melt adhesive is a copolymer of ethylene and at least one branched or unbranched 1-olefin having from 3 to 20 carbon atoms, with the content of structural units derived from ethylene being from 70 to 99.9% by weight.

In a particularly preferred embodiment of the invention, the polyolefin present in the hot melt adhesive is a copolymer of propylene with from 0.1 to 30% by weight, in particular from 1 to 20% by weight, of ethylene.

The hot melt adhesive of the invention preferably contains the polyolefin or polyolefins in an amount of from 2 to 100% by weight, preferably from 30 to 95% by weight, particularly preferably from 50 to 85% by weight, very particularly preferably from 70 to 80% by weight.

The hot melt adhesive of the invention additionally contains one or more tackifier(s) selected from the group of resins. Aliphatic and cycloaliphatic or aromatic hydrocarbon resins are possible. These can be prepared by polymerization of particular resin oil fractions obtained in the refining of petroleum. Such resins, which can, for example, be modified by hydrogenation or functionalization, are obtainable, for example, under the trade names Eastoflex, RegalREZ, Kristalex, Eastotac, Piccotac (Eastman Chemical Company) or Escorez (ExxonMobil Chemical Company). Further possible resins are polyterpene resins prepared by polymerization of terpenes, for example pinene, in the presence of Friedel-Crafts catalysts, likewise hydrogenated polyterpenes, copolymers and terpolymers of natural terpenes, for example styrene-terpene or α-methylstyrene-terpene copolymers. Further possibilities are natural and modified rosins, in particular resin esters, glyceryl esters of tree resins, pentaerithrityl esters of tree resins and tall oil resins and hydrogenated derivatives thereof and also phenol-modified pentaerithrityl esters of resins and phenol-modified terpene resins.

The resins mentioned are present in the hot melt adhesive of the invention either individually or in any combination in amounts, based on the total weight of the hot melt adhesive, in the range from 0 to 60% by weight, preferably from 10 to 50% by weight, particularly preferably from 15 to 30% by weight.

In a very particularly preferred embodiment of the invention, the hot melt adhesive contains one or more of the above-described polyolefins and additionally a tackifier selected from among amorphous poly-alpha-olefins, e.g. of the grades of the Vestoplast® series (Degussa) or the "Rextac" grades from Huntsman, aliphatic, cycloaliphatic or aromatic hydrocarbon resins as are obtainable, for example, under the trade name "Escorez" from ExxonMobil, also polyisobutylene obtainable, for example, under the trade name "Oppanol" from BASF. Furthermore, other polyolefins such as low-pressure polyethylenes as are available, for example, under the name "Affinity" from Dow Chemical can also be present, also high-pressure polyethylenes including those containing polar comonomers, e.g. ethylene-vinyl acetate. The total mixture of the hot melt adhesive obtained in this way has a viscosity in the range from 100 to 10 000 mPa·s at 170° C., preferably from 120 to 9000 mPa·s at 170° C., particularly preferably from 130 to 8000 mPa·s at 170° C. If appropriate, pigments, antioxidants, odor binders, antimicrobial agents or colorants and fragrances can additionally be present.

The hot melt adhesive of the invention is used in the production of various hygiene articles such as diapers, panty diapers, incontinence products, panty liners and sanitary towels, in particular for laminating fiber materials such as nonwoven materials to film.

According to the invention, the hot melt adhesive of the invention is used in amounts of from 1 to 6 g/m$^2$, preferably from 3 to 5.5 g/m$^2$, for adhesively bonding nonwoven to film.

As fibrous materials, in particular as nonwoven materials, preferably for diaper nonwovens, for total diaper construction and for incontinence products, it is possible to use natural or synthetic fiber materials composed of, for example, cotton, wool, silk, cellulose, linen, polyamide, for example Nylon or Perlon, polyester, for example polyethylene terephthalate or polypropylene terephthalate, polyvinyl chloride, polypropylene, polyethylene and also mixtures of these materials.

The films can comprise customary materials such as polyethylene terephthalate, polycarbonate, polyethylene, polypropylene, polyvinyl chloride or polystyrene, but the hot melt adhesive of the invention is also suitable for joining fibrous materials to metal surfaces composed of aluminum or iron-containing metals.

It is also possible to use woven textiles as fibrous materials. In particular, such woven textiles can be adhesively bonded to one another or to nonwoven material or films.

The invention further provides hygiene articles, preferably diapers, incontinence products, panty liners and sanitary towels, containing the hot melt adhesive of the invention.

The metallocene polyolefins present in the hot melt adhesive of the invention are prepared using metallocene compounds of the formula I as catalysts.

(I)

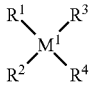

This formula also encompasses compounds of the formula Ia, (Ia)

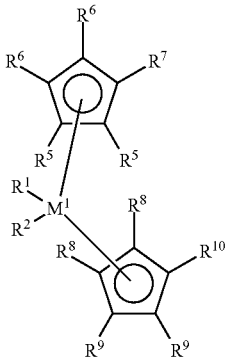

of the formula Ib, (Ib)

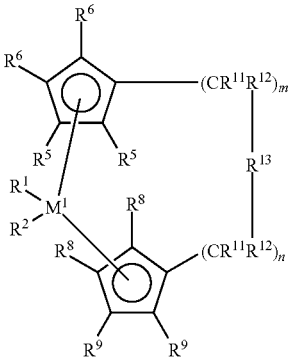

and of the formula Ic.

(Ic)

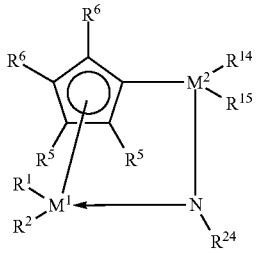

In the formulae I, Ia and Ib, $M^1$ is a metal of group IVb, Vb or VIb of the Periodic Table, for example titanium, zirconium, hafnium, vanadium, niobium, tantalum, chromium, molybdenum, tungsten, preferably titanium, zirconium and hafnium.

$R^1$ and $R^2$ are identical or different and are each a hydrogen atom, a $C_1$-$C_{10}$-, preferably $C_1$-$C_3$-alkyl group, in particular methyl, a $C_1$-$C_{10}$-, preferably $C_1$-$C_3$-alkoxy group, a $C_6$-$C_{10}$-, preferably $C_6$-$C_8$-aryl group, a $C_6$-$C_{10}$-, preferably $C_6$-$C_8$-aryloxy group, a $C_2$-$C_{10}$-, preferably $C_2$-$C_4$-alkenyl group, a $C_7$-$C_{40}$-, preferably $C_7$-$C_{10}$-arylalkyl group, a $C_7$-$C_{40}$-, preferably $C_7$-$C_{12}$-alkylaryl group, a $C_8$-$C_{40}$-, preferably $C_8$-$C_{12}$-arylalkenyl group or a halogen, preferably chlorine atom.

$R^3$ and $R^4$ are identical or different and are each a monocyclic or polycyclic hydrocarbon radical which can form a sandwich structure with the central atom $M^1$. $R^3$ and $R^4$ are preferably cyclopentadienyl, indenyl, tetrahydroindenyl, benzoindenyl or fluorenyl, with the basic molecules also being able to bear additional substituents or be bridged to one another. In addition, one of the radicals $R^3$ and $R^4$ can be a substituted nitrogen atom, where $R^{24}$ has the meaning of $R^{17}$ and is preferably methyl, tert-butyl or cyclohexyl.

$R^5$, $R^6$, $R^7$, $R^8$, $R^9$ and $R^{10}$ are identical or different and are each a hydrogen atom, a halogen atom, preferably a fluorine, chlorine or bromine atom, a $C_1$-$C_{10}$, preferably $C_1$-$C_4$-alkyl group, a $C_6$-$C_{10}$-, preferably $C_6$-$C_8$-aryl group, a $C_1$-$C_{10}$-, preferably $C_1$-$C_3$-alkoxy group, a $—NR^{16}{}_2$, $—SR^{16}$, $—OSiR^{16}{}_3$, $—SiR^{16}$ or $—PR^{16}{}_2$ radical, where $R^{16}$ is a $C_1$-$C_{10}$-, preferably $C_1$-$C_3$-alkyl group or a $C_6$-$C_{10}$-, preferably $C_6$-$C_8$-aryl group or in the case of Si- or P-containing radicals can also be a halogen atom, preferably a chlorine atom, or two adjacent radicals $R^5$, $R^6$, $R^7$, $R^8$, $R^9$ or $R^{10}$ together with the carbon atoms connecting them form a ring. Particularly preferred ligands are the substituted compounds of the basic molecules cyclopentadienyl, indenyl, tetrahydroindenyl, benzoindenyl or fluorenyl.

$R^{13}$ is

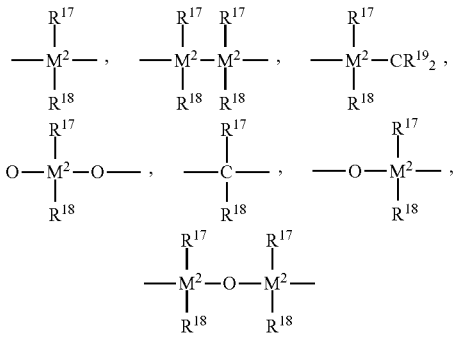

$=BR^{17}$, $=AlR^{17}$, —Ge—, —Sn—, —O—, —S—, =SO, $=SO_2$, $=NR^{17}$, =CO, $=PR^{17}$ or $=P(O)R^{17}$, where $R^{17}$, $R^{18}$ and $R^{19}$ are identical or different and are each a hydrogen atom, a halogen atom, preferably a fluorine, chlorine or bromine atom, a $C_1$-$C_{30}$-, preferably $C_1$-$C_4$-alkyl group, in particular a methyl group, a $C_1$-$C_{10}$-fluoroalkyl, preferably $CF_3$ group, a $C_6$-$C_{10}$-fluoroaryl group, preferably a pentafluorophenyl group, a $C_6$-$C_{10}$-, preferably $C_6$-$C_8$-aryl group, a $C_1$-$C_{10}$-, preferably $C_1$-$C_4$-alkoxy group, in particular a methoxy group, a $C_2$-$C_{10}$-, preferably $C_2$-$C_4$-alkenyl group, a $C_7$-$C_{40}$-, preferably $C_7$-$C_{10}$-aralkyl group, a $C_8$-$C_{40}$-, preferably $C_8$-$C_{12}$-arylalkenyl group or a $C_7$-$C_{40}$-, preferably $C_7$-$C_{12}$-alkylaryl group, or $R^{17}$ and $R^{18}$ or $R^{17}$ and $R^{19}$ in each case together with the atoms connecting them form a ring.

$M^2$ is silicon, germanium or tin, preferably silicon or germanium. $R^{13}$ is preferably $=CR^{17}R^{18}$, $=SiR^{17}R^{18}$, $=GeR^{17}R^{18}$, —O—, —S—, =SO, $=PR^{17}$ or $=P(O)R^{17}$.

$R^{11}$ and $R^{12}$ are identical or different and have the meaning given for $R^{17}$. m and n are identical or different and are each zero, 1 or 2, preferably zero or 1, where m plus n is zero, 1 or 2, preferably zero or 1.

$R^{14}$ and $R^{15}$ have the meanings of $R^{17}$ and $R^{18}$.

Specific examples of suitable metallocenes are:

bis(1,2,3-trimethylcyclopentadienyl)zirconium dichloride, bis(1,2,4-trimethylcyclopentadienyl)zirconium dichloride, bis(1,2-dimethylcyclopentadienyl)zirconium dichloride, bis(1,3-dimethylcyclopentadienyl)zirconium dichloride, bis(1-methylindenyl)zirconium dichloride, bis(1-n-butyl-3-methylcyclopentadienyl)zirconium dichloride, bis(2-methyl-4,6-di-i-propylindenyl)zirconium dichloride, bis(2-methylindenyl)zirconium dichloride, bis(4-methylindenyl)zirconium dichloride, bis(5-methylindenyl)zirconium dichloride, bis(alkylcyclopentadienyl)zirconium dichloride, bis(alkylindenyl)zirconium dichloride, bis(cyclopentadienyl)zirconium dichloride, bis(indenyl)zirconium dichloride, bis(methylcyclopentadienyl)zirconium dichloride, bis(n-butylcyclopentadienyl)zirconium dichloride, bis(octadecylcyclopentadienyl)zirconium dichloride, bis(pentamethylcyclopentadienyl)zirconium dichloride, bis(trimethylsilylcyclopentadienyl)zirconium dichloride, biscyclopentadienyldibenzylzirconium, biscyclopentadienyldimethylzirconium, bistetrahydroindenylzirconium dichloride, dimethylsilyl-9-fluorenylcyclopentadienylzirconium dichloride, dimethylsilylbis-1-(2,3,5-trimethylcyclopentadienyl)zirconium dichloride, dimethylsilylbis-1-(2,4-dimethylcyclopentadienyl)zirconium dichloride, dimethylsilylbis-1-(2-methyl-4,5-benzoindenyl)zirconium dichloride, dimethylsilylbis-1-(2-methyl-4-ethylindenyl)zirconium dichloride, dimethylsilylbis-1-(2-methyl-4-i-propylindenyl)zirconium dichloride, dimethylsilylbis-1-(2-methyl-4-phenylindenyl)zirconium dichloride, dimethylsilylbis-1-(2-methylindenyl)zirconium dichloride, dimethylsilylbis-1-(2-methyltetrahydroindenyl)zirconium dichloride, dimethylsilylbis-1-indenylzirconium dichloride, dimethylsilylbis-1-indenyldimethylzirconium, dimethylsilylbis-1-tetrahydroindenylzirconium dichloride, diphenylmethylene-9-fluorenylcyclopentadienylzirconium dichloride, diphenylsilylbis-1-indenylzirconium dichloride, ethylenebis-1-(2-methyl-4,5-benzoindenyl)zirconium dichloride, ethylenebis-1-(2-methyl-4-phenylindenyl)zirconium dichloride, ethylenebis-1-(2-methyltetrahydroindenyl)zirconium dichloride, ethylenebis-1-(4,7-dimethylindenyl)zirconium dichloride, ethylenebis-1-indenylzirconium dichloride, ethylenebis-1-tetrahydroindenylzirconium dichloride, indenylcyclopentadienylzirconium dichloride, isopropylidene(1-indenyl)(cyclopentadienyl)zirconium dichloride, isopropylidene(9-fluorenyl)(cyclopentadienyl)zirconium dichloride, phenylmethylsilylbis-1-(2-methylindenyl)zirconium dichloride, and also the alkyl or aryl derivatives of each of these metallocene dichlorides.

To activate the single-site catalyst systems, use is made of suitable cocatalysts. Suitable cocatalysts for metallocenes of the formula I are organoaluminum compounds, in particular aluminoxanes or else aluminum-free systems such as $R^{20}_xNH_{4-x}BR^{21}_4$, $R^{20}_xPH_{4-x}BR^{21}_4$, $R^{20}_3CBR^{21}_4$ or $BR^{21}_3$. In these formulae, x is from 1 to 4, the radicals $R^{20}$ are identical or different, preferably identical, and are each $C_1$-$C_{10}$-alkyl or $C_6$-$C_{18}$-aryl or two radicals $R^{20}$ together with the atom connecting them form a ring and the radicals $R^{21}$ are identical or different, preferably identical, and are each $C_6$-$C_{18}$-aryl which may be substituted by alkyl, haloalkyl or fluorine. In particular, $R^{20}$ is ethyl, propyl, butyl or phenyl and $R^{21}$ is phenyl, pentafluorophenyl, 3,5-bistrifluoromethylphenyl, mesityl, xylyl or tolyl.

In addition, a third component is frequently necessary to maintain protection against polar catalyst poisons. Organoaluminum compounds such as triethylaluminum, tributylaluminum and others and also mixtures of these are suitable for this purpose.

Depending on the process, it is also possible to use supported single-site catalysts. Preference is given to catalyst systems in which the residual contents of support material and cocatalyst do not exceed a concentration of 100 ppm in the product.

Processes for preparing such polyolefins are described in the prior art, for example EP-A-0 321 851, EP-A-0 321 852, EP-A-0 384 264, EP-A-0 571 882 and EP-A-0 890 584.

EXAMPLES

The following examples illustrate the invention but do not restrict it to the specific embodiments described.

Percentages are, unless indicated otherwise, by weight.

The melt viscosities were determined in accordance with DIN 53019 using a rotational viscosimeter, the dropping points were determined in accordance with ASTM D3954, the ring/ball softening points were determined in accordance with ASTM D3104. The weight average molar mass $M_w$ and the number average molar mass $_n$ were determined by gel permeation chromatography at a temperature of 135° C. in 1,2-dichloro-benzene.

The polyolefins 1 to 4 which were used according to the invention and are shown in Table 1 were prepared by methods of the prior art as described in EP 0 384 264 or EP 0 571 882.

TABLE 1

| Polyolefins used | | | | |
|---|---|---|---|---|
| | Polyolefin 1 | Polyolefin 2 | Polyolefin 3 | Polyolefin 4 |
| Preparation according to | EP 0 384 264 general method Ex. 1-16[1)] | EP 0 384 264 general method Ex. 1-16[2)] | EP 0 571 882 Ex. 3 | EP 0 384 264 general method Ex. 1-16[3)] |
| Type | Propylene-ethylene copolymer | Propylene-ethylene copolymer | Propylene homopolymer | Propylene-ethylene copolymer |
| Softening point (° C.) | 83[4)] | 88 | 145[4)] | 106 |
| Viscosity at 170° C. (mPa · s) | 180 | 11500 | 101 | 4300 |
| $M_n$ | 2760 | 8250 | 1980 | 5320 |
| $M_w$ | 6320 | 19110 | 3900 | 12030 |

[1)]Polymerization data: total ethylene usage 400 g, polymerization temp. 75° C.
[2)]Total ethylene usage 350 g, polymerization temp. 65° C.
[3)]Total ethylene usage 200 g, polymerization temp. 50° C.
[4)]Dropping point The polyolefins 1 to 4 which are described in detail above were melted together with the additional components shown in Table 2 in the mixing ratios indicated and mixed at a temperature of 170° C.

TABLE 2

Illustrative formulations and comparative formulations (reported in % by weight) and resulting initial peel values in N/mm$^2$, measured at 37° C.

| | Example | | | | |
|---|---|---|---|---|---|
| | 1 | 2 | 3 | 4 | 5 |
| Polyolefin 1 | 80 | | | | |
| Polyolefin 2 | | 80 | | | |
| Polyolefin 3 | | | 5 | | |
| Polyolefin 4 | | | 75 | 80 | |
| Affinity GA-1900 | | | | | 60 |
| Escorez 5637 | 20 | 20 | 20 | 20 | 40 |
| Oppanol B11 | | | | | |
| Vestoplast 828 | | | | | |
| Initial peel | — | 364 | 544 | — | 205 |

| | Example | | | | |
|---|---|---|---|---|---|
| | 6 | 7 | 8 | 9 | 10 |
| Comparison I SIS based | 100 | | | | |
| Comparison II SIS based | | 100 | | | |
| Huntsman RT-2730 | | | 100 | | |
| Polyolefin 3 | | | | 70 | 30 |
| Escorez 5400 | | | | | 40 |
| Escorez 5637 | | | | 20 | |
| Oppanol B11 | | | | 10 | |
| Vestoplast 828 | | | | | 30 |
| Initial peel | 192 | 205 | 166 | 473 | 392 |

To determine the peel values of the hot melt adhesives tested, nonwoven material BBA Style 717D (16.9 gsm) was adhesively bonded to a polyethylene film Clopay DH-203 PE by means of each of the hot melt adhesives as per illustrative formulations 1 to 10 at 25° C., with in each case 6.2 g/m$^2$ of hot melt adhesive being sprayed onto the nonwoven material and the sprayed nonwoven and the film then being promptly pressed together by means of rollers. The specimens were stored for 24 hours at a temperature of 25° C. under standard conditions and then peeled at a speed of 12 inches/min and a peel angle of 180° at 25° C.

The test results show, by way of the initial peel values, a sometimes very large increase in the adhesive strength of the hot melt adhesives containing the polyolefins used according to the invention, compared to hot melt adhesives of the prior art (see Examples 5, 6, 7 and 8). Consequently, a satisfactory adhesive action can be achieved even when using the hot melt adhesives of the invention in amounts of less than 6 g/m$^2$.

Chemical nature of the commercial products used:

| | |
|---|---|
| Affinity GA-1900 | Polyethylene (Dow Chemical Corp.) |
| Escorez 5637 | Hydrocarbon resin (ExxonMobil) |
| Escorez 5400 | Hydrocarbon resin (ExxonMobil) |
| Oppanol B11 | Polyisobutene (BASF) |
| Vestoplast 828 | amorphous poly-alpha-olefin (Degussa) |
| Huntsman RT-2730 | amorphous poly-alpha-olefin (Huntsmann) |
| Comparison I SIS based | hot melt adhesive formulation comprising styrene-isoprene block copolymer, oil, resin (H B Fuller) |
| Comparison II SIS based | hot melt adhesive formulation comprising styrene-isoprene block copolymer, oil, resin (National Starch) |

The invention claimed is:

[1. A hot melt adhesive for adhesively bonding fibrous materials to one another or to smooth substrate surfaces, comprising at least one polyolefin prepared by polymerization in the presence of metallocene as catalyst and has a ring/ball softening point in the range from 50 to 165° C. and a melt viscosity measured at a temperature of 170° C. in the range from 100 to 20,000 mPa·s, wherein the at least one polyolefin is a copolymer of propylene with at least one or more further monomers selected from the group consisting of ethylene and linear or branched 1-olefins having from 4 to 20 carbon atoms, with the content of structural units derived from propylene being from 70 to 99.9% by weight and wherein the hot melt adhesive is free of plasticators, plasticizers or both.**]

2. The [hot melt adhesive] *hygiene article, panty diaper, diaper, incontinence product, panty liner or sanitary towel* as claimed in claim [1] *12*, wherein the at least one polyolefin has a glass transition temperature $T_g$ of not more than −10° C. and a melt flow index MFI of greater than 30 g/10 min, measured in accordance with ISO 1133 at a temperature of 190° C. and under a load of 2.16 kg.

3. The [hot melt adhesive] *method* as claimed in claim [1] *8*, wherein the hot melt adhesive is water- and solvent-free.

4. The [hot melt adhesive] *hygiene article, panty diaper, diaper, incontinence product, panty liner or sanitary towel* as claimed in claim [1] *12*, wherein the at least one polyolefin is present in an amount of from 2 to 100% by weight.

5. The [hot melt adhesive] *hygiene article, panty diaper, diaper, incontinence product, panty liner or sanitary towel* as claimed in claim [1] *12*, further comprising one or more tackifiers selected from the group of resins consisting of aliphatic, cycloaliphatic or aromatic hydrocarbon resins, polyterpene resins prepared by polymerization of terpenes in the presence of Friedel-Crafts catalysts, hydrogenated polyterpenes, copolymers and terpolymers of natural terpenes, styrene-terpene, α-methylstyrene-terpene copolymers, natural resins, modified rosins, resin esters, glyceryl esters of tree resins, pentaerithrityl esters of tree resins, tall oil resins and hydrogenated derivatives thereof, phenol-modified pentaerithrityl esters of resins and phenol-modified terpene resins and amorphous poly-alpha-olefins.

6. The [hot melt adhesive] *hygiene article, panty diaper, diaper, incontinence product, panty liner or sanitary towel* as claimed in claim [1] *12*, wherein the hot melt adhesive contains at least one [of] *additional* resin in an amount, based on the total weight of the hot melt adhesive, in the range from 0 to 60% by weight and wherein *the at least one additional resin is selected from the group consisting of* aliphatic, cycloaliphatic or aromatic hydrocarbon resins.

7. The [hot melt adhesive] *hygiene article, panty diaper, diaper, incontinence product, panty liner or sanitary towel* as claimed in claim [1] *12*, further comprising at least one constituent selected from the group consisting of pigments, antioxidants, odor binders, antimicrobial agents, colorants and fragrances.

8. A method for laminating fiber materials *of a hygiene article, panty diaper, diaper, incontinence product, panty liner or sanitary towel as claimed in claim 12* to one another, comprising the step of applying a hot melt adhesive between the fiber materials, wherein the holt melt adhesive comprises at least one polyolefin prepared by polymerization in the presence of metallocene as catalyst and has a ring/ball softening point in the range from 50 to 165° C. and a melt viscosity measured at a temperature of 170° C. in the range from 100 to 20,000 mPa·s, wherein the at least one polyolefin is a copolymer of propylene with at least one or more further monomers selected from the group consisting of ethylene and linear or branched 1-olefins having from 4 to 20 carbon atoms, with the content of structural units derived from propylene being from 70 to 99.9% by weight and wherein the hot melt adhesive is free of [plasticators,] plasticizers [or both].

9. The method as claimed in claim 8, wherein the hot melt adhesive is applied in an amount of from 1 to 6 g/m$^2$.

10. The method as claimed in claim 8, wherein fiber material is selected from the group consisting of cotton, wool, silk, cellulose, linen, polyamide, polyester, polyethylene terephthalate, polypropylene terephthalate, polyvinyl chloride, propylene, polyethylene or mixtures thereof.

[11. The method as claimed in claim 8, wherein the film is selected from the group consisting of polyethylene terephthalate, polycarbonate, polyethylene, polypropylene, polyvinyl chloride and polystyrene.]

12. A hygiene article, a panty diaper, diaper, incontinence product, panty liner or sanitary towel comprising a hot melt adhesive, wherein the holt melt adhesive comprises at least one polyolefin prepared by polymerization in the presence of metallocene as catalyst and has a ring/ball softening point in the range from 50 to 165° C. and a melt viscosity measured at a temperature of 170° C. in the range from 100 to 20,000 mPa·s, wherein the at least one polyolefin is a copolymer of propylene with at least one or more further monomers selected from the group consisting of ethylene and linear or branched 1-olefins having from 4 to 20 carbon atoms, with the content of structural units derived from propylene being from 70 to 99.9% by weight and wherein the hot melt adhesive is free of [plasticators,] plasticizers [or both].

[13. The hot melt adhesive as claimed in claim 1, wherein the at least one polyolefin has a melt viscosity measured at a temperature of 170° C. in the range from 100 to 20 000 mPa·s.]

14. The [hot melt adhesive] *hygiene article, panty diaper, diaper, incontinence product, panty liner or sanitary towel* as claimed in [one] claim [1] *12*, wherein the at least one polyolefin has a number average molar mass $M_n$ in the range from 800 to 10 000 g/mol, and a weight average molar mass $M_w$ in the range from 1600 to 30 000 g/mol.

15. The [hot melt adhesive] *hygiene article, panty diaper, diaper, incontinence product, panty liner or sanitary towel* as claimed in [one] claim [1] *12*, wherein the at least one polyolefin has a number average molar mass $M_n$ in the range from 1000 to 5000 g/mol, and a weight average molar mass $M_w$ in the range from 2000 to 20 000 g/mol.

16. The [hot melt adhesive] *hygiene article, panty diaper, diaper, incontinence product, panty liner or sanitary towel* as claimed in claim [1] *12*, wherein the linear or branched 1-olefins having from 4 to 10 carbon atoms.

17. The [hot melt adhesive] *hygiene article, panty diaper, diaper, incontinence product, panty liner or sanitary towel* as claimed in claim [1] *12*, wherein the content of structural units derived from propylene being from 80 to 99% by weight.

18. The [hot melt adhesive] *hygiene article, panty diaper, diaper, incontinence product, panty liner or sanitary towel* as claimed in claim [1] *12*, wherein the at least one polyolefin is present in an amount of from 30 to 95% by weight.

19. The [hot melt adhesive] *hygiene article, panty diaper, diaper, incontinence product, panty liner or sanitary towel* as claimed in claim [1] *12*, wherein the at least one polyolefin is present in an amount of from 50 to 85% by weight.

20. The [hot melt adhesive] *hygiene article, panty diaper, diaper, incontinence product, panty liner or sanitary towel* as claimed in claim [1] *12*, wherein the at least one polyolefin is present in an amount of from 70 to 80% by weight.

21. The [hot melt adhesive] *hygiene article, panty diaper, diaper, incontinence product, panty liner or sanitary towel* as claimed in claim [1] *12*, wherein the hot melt adhesive contains at least one [of] *additional* resin in an amount, based on the total weight of the hot melt adhesive, in the range from 10 to 50% by weight.

22. The [hot melt adhesive] *hygiene article, panty diaper, diaper, incontinence product, panty liner or sanitary towel* as claimed in claim [1] *12*, wherein the hot melt adhesive contains at least one [of] *additional* resin in an amount, based on the total weight of the hot melt adhesive, in the range from 15 to 30% by weight.

23. A diaper, panty diaper, incontinence product, panty liner or sanitary towel produced with a hot melt adhesive, wherein the holt melt adhesive comprises at least one polyolefin prepared by polymerization in the presence of metallocene as catalyst and has a ring/ball softening point in the range from 50 to 165° C. and a melt viscosity measured at a temperature of 170° C. in the range from 100 to 20,000 mPa·s, wherein the at least one polyolefin is a copolymer of propylene with at least one or more further monomers selected from the group consisting of ethylene and linear or branched 1-olefins having from 4 to 20 carbon atoms, with the content of structural units derived from propylene being from 70 to 99.9% by weight and wherein the hot melt adhesive is free of [plasticators,] plasticizers [or both].

24. The method as claimed in claim 8, wherein the hot melt adhesive is applied in an amount of from 3 to 5.5 g/m2.

*25. A hygiene article comprising a first fiber material laminated by adhesive bonding to a film or to a second fiber material by a hot melt adhesive disposed between and in contact with the first fiber material and the film or the second fiber material, the laminated first fiber material and film or second fiber material forming part of the hygiene article, wherein the hot melt adhesive comprises at least one polyolefin prepared by polymerization in the presence of metallocene as catalyst and having a ring/ball softening point in the range from 50 to 165° C. and a melt viscosity measured at a temperature of 170° C. in the range from 100 to 20,000 mPa·s, wherein the at least one polyolefin is a copolymer of propylene and ethylene with the content of structural units derived from propylene being from 70 to 99.9% by weight, and wherein the hot melt adhesive is free of plasticizers.*

*26. The hygiene article as claimed in claim 25, wherein the at least one polyolefin has a glass transition temperature $T_g$ of not more than −10° C. and a melt flow index MFI of greater than 30 g/10 min, measured in accordance with ISO 1133 at a temperature of 190° C. and under a load of 2.16 kg.*

*27. The hygiene article as claimed in claim 25, wherein the hot melt adhesive is water- and solvent-free.*

*28. The hygiene article as claimed in claim 25, wherein the hot melt adhesive has a viscosity in the range of 200 to 10000 mPa·s measured at a temperature of 150° C.*

*29. The hygiene article as claimed in claim 25, wherein the hot melt adhesive has a viscosity in the range of 120 to 9000 mPa·s measured at a temperature of 170° C.*

*30. The hygiene article as claimed in claim 25, wherein the hot melt adhesive has a viscosity in the range of 130 to 8000 mPa·s measured at a temperature of 170° C.*

*31. The hygiene article as claimed in claim 25, wherein the at least one polyolefin has a number average molar mass $M_n$ in the range from 500 to 20000 g/mol, and a weight average molar mass $M_w$ in the range from 1000 to 40000 g/mol.*

*32. The hygiene article as claimed in claim 25, wherein the at least one polyolefin has a number average molar mass $M_n$ in the range from 800 to 10000 g/mol, and a weight average molar mass $M_w$ in the range from 1600 to 30000 g/mol.*

*33. The hygiene article as claimed in claim 25, wherein the at least one polyolefin has a number average molar mass $M_n$ in the range from 1000 to 5000 g/mol, and a weight average molar mass $M_w$ in the range from 2000 to 20000 g/mol.*

*34. The hygiene article as claimed in claim 25, wherein in the at least one polyolefin the content of structural units derived from propylene is from 80 to 99% by weight.*

*35. The hygiene article as claimed in claim 25, wherein the at least one polyolefin is present in an amount of from 30 to 95% by weight.*

*36. The hygiene article as claimed in claim 35, wherein the at least one polyolefin has a number average molar mass $M_n$ in the range from 500 to 20000 g/mol, and a weight average molar mass $M_w$ in the range from 1000 to 40000 g/mol.*

*37. The hygiene article as claimed in claim 25, wherein the at least one polyolefin is present in an amount of from 50 to 85% by weight.*

*38. The hygiene article as claimed in claim 25, wherein the at least one polyolefin is present in an amount of from 70 to 80% by weight.*

*39. The hygiene article as claimed in claim 25, wherein the hot melt adhesive further comprises at least one tackifier resin in an amount, based on the total weight of the hot melt adhesive, up to 60% by weight.*

*40. The hygiene article as claimed in claim 25, wherein the hot melt adhesive further comprises at least one tackifier resin in an amount, based on the total weight of the hot melt adhesive, in the range from 10 to 50% by weight.*

*41. The hygiene article as claimed in claim 40, wherein the at least one tackifier resin is at least one aliphatic, cycloaliphatic or aromatic hydrocarbon resin.*

*42. The hygiene article as claimed in claim 40, wherein the at least one tackifier resin is at least one resin selected from the group consisting of polyterpene resins prepared by polymerization of terpenes in the presence of Friedel-Crafts catalysts, hydrogenated polyterpenes, copolymers and terpolymers of natural terpenes, styrene-terpene, α-methylstyrene-terpene copolymers, natural resins, modified rosins, resin esters, glyceryl esters of tree resins, pentaerithrityl esters of tree resins, tall oil resins and hydrogenated derivatives thereof, phenol-modified pentaerithrityl esters of resins and phenol-modified terpene resins and amorphous poly-alpha-olefins.*

*43. The hygiene article as claimed in claim 40, wherein the at least one polyolefin is present in an amount of from 50 to 85% by weight, and wherein the at least one polyolefin has a number average molar mass $M_n$ in the range from 500 to 20000 g/mol, and a weight average molar mass $M_w$ in the range from 1000 to 40000 g/mol.*

*44. The hygiene article as claimed in claim 25, wherein the hot melt adhesive further comprises at least one tackifier resin in an amount, based on the total weight of the hot melt adhesive, in the range from 15 to 30% by weight.*

*45. The hygiene article as claimed in claim 25, wherein*

*the at least one polyolefin has a number average molar mass $M_n$ in the range from 800 to 10000 g/mol, and a weight average molar mass $M_w$ in the range from 1600 to 30000 g/mol;*

*the at least one polyolefin is present in the hot melt adhesive in an amount of from 50 to 85% by weight;*

*wherein the hot melt adhesive has a viscosity in the range of 130 to 8000 mPa·s measured at a temperature of 170° C.; and*

*the hot melt adhesive is water- and solvent-free.*

*46. The hygiene article as claimed in claim 45, wherein the hot melt adhesive further comprises at least one tackifier resin in an amount, based on the total weight of the hot melt adhesive, in the range from 10 to 50% by weight, the at least one tackifier resin being at least one aliphatic, cycloaliphatic or aromatic hydrocarbon resin.*

*47. The hygiene article as claimed in claim 46, wherein in the at least one polyolefin the content of structural units derived from propylene is from 80 to 99% by weight.*

*48. The hygiene article as claimed in claim 45, wherein in the at least one polyolefin the content of structural units derived from propylene is from 80 to 99% by weight.*

*49. The hygiene article as claimed in claim 48, wherein the at least one polyolefin has a glass transition temperature $T_g$ of not more than −10° C. and a melt flow index MFI of greater than 30 g/10 min, measured in accordance with ISO 1133 at a temperature of 190° C. and under a load of 2.16 kg.*

*50. The hygiene article as claimed in claim 25, wherein the hot melt adhesive is disposed between and in contact with the first fiber material and the second fiber material and laminating the first fiber material to the second fiber material.*

*51. The hygiene article as claimed in claim 50, wherein the first fiber material is selected from the group consisting of cotton, wool, silk, cellulose, linen, polyamide, polyester, polyethylene terephthalate, polypropylene terephthalate, polyvinyl chloride, propylene, polyethylene or mixtures thereof; and the second fiber material is selected from the group consisting of cotton, wool, silk, cellulose, linen, polyamide, polyester, polyethylene terephthalate, polypropylene terephthalate, polyvinyl chloride, propylene, polyethylene or mixtures thereof.*

*52. The hygiene article as claimed in claim 35, wherein the hot melt adhesive is disposed between and in contact with the first fiber material and the second fiber material and laminating the first fiber material to the second fiber material.*

*53. The hygiene article as claimed in claim 36, wherein the hot melt adhesive is disposed between and in contact with the first fiber material and the second fiber material and laminating the first fiber material to the second fiber material.*

*54. The hygiene article as claimed in claim 45, wherein the hot melt adhesive is disposed between and in contact with the first fiber material and the second fiber material and laminating the first fiber material to the second fiber material.*

*55. The hygiene article as claimed in claim 35, wherein the hot melt adhesive is disposed between and in contact with the first fiber material and the film and laminating the first fiber material to the film.*

*56. The hygiene article as claimed in claim 49, wherein the hot melt adhesive is disposed between and in contact with the first fiber material and the film and laminating the first fiber material to the film.*

*57. A method for making the hygiene article as claimed in claim 25, the method comprising laminating the first fiber material to the second fiber material by disposing the hot melt adhesive between and in contact with the first fiber material and the second fiber material.*

*58. The method as claimed in claim 57, wherein the hot melt adhesive is disposed between the first fiber material and the second fiber material in an amount in the range of from 1 to 6 g/m$^2$.*

*59. A method for making the hygiene article as claimed in claim 26, the method comprising laminating the first fiber material to the second fiber material by disposing the hot melt adhesive between and in contact with the first fiber material and the second fiber material.*

*60. The method as claimed in claim 59, wherein the hot melt adhesive is disposed between the first fiber material and the second fiber material in an amount in the range of from 1 to 6 g/m$^2$.*

*61. A method for making the hygiene article as claimed in claim 35, the method comprising laminating the first fiber material to the second fiber material by disposing the hot melt adhesive between and in contact with the first fiber material and the second fiber material.*

*62. A method for making the hygiene article as claimed in claim 36, the method comprising laminating the first fiber material to the second fiber material by disposing the hot melt adhesive between and in contact with the first fiber material and the second fiber material.*

*63. A method for making the hygiene article as claimed in claim 49, the method comprising laminating the first fiber material to the second fiber material by disposing the hot melt adhesive between and in contact with the first fiber material and the second fiber material.*

*64. The hygiene article as claimed in claim 25, wherein the first fiber material is laminated to the film by the hot melt adhesive.*

*65. The hygiene article as claimed in claim 64, first the hot melt adhesive is disposed between the first fiber material and the film in an amount in the range of from 1 to 6 g/m$^2$.*

*66. The hygiene article as claimed in claim 64, wherein the first fiber material is selected from the group consisting of cotton, wool, silk, cellulose, linen, polyamide, polyester, polyethylene terephthalate, polypropylene terephthalate, polyvinyl chloride, propylene, polyethylene or mixtures thereof, and wherein the film is a film of a material selected from the group consisting of polyethylene terephthalate, polycarbonate, polyethylene, polypropylene, polyvinyl chloride and polystyrene.*

*67. The hygiene article as claimed in claim 64, wherein the hygiene article is in the form of a panty diaper, a diaper, an incontinence product, a panty liner, or a sanitary towel.*

*68. The hygiene article as claimed in claim 26, wherein the first fiber material is laminated to the film by the hot melt adhesive.*

*69. The hygiene article as claimed in claim 68, wherein the hot melt adhesive is disposed between the first fiber material and the film in an amount in the range of from 1 to 6 g/m$^2$.*

*70. The hygiene article as claimed in claim 68, wherein the first fiber material is selected from the group consisting of cotton, wool, silk, cellulose, linen, polyamide, polyester, polyethylene terephthalate, polypropylene terephthalate, polyvinyl chloride, propylene, polyethylene or mixtures thereof, and wherein the film is a film of a material selected from the group consisting of polyethylene terephthalate, polycarbonate, polyethylene, polypropylene, polyvinyl chloride and polystyrene.*

*71. The hygiene article as claimed in claim 70, wherein the hygiene article is in the form of a panty diaper, a diaper, an incontinence product, a panty liner, or a sanitary towel.*

*72. The hygiene article as claimed in claim 36, wherein the first fiber material is laminated to the film by the hot melt adhesive.*

*73. The hygiene article as claimed in claim 72, first the hot melt adhesive is disposed between the first fiber material and the film in an amount in the range of from 1 to 6 g/m$^2$.*

*74. The hygiene article as claimed in claim 72, wherein the first fiber material is selected from the group consisting of cotton, wool, silk, cellulose, linen, polyamide, polyester, polyethylene terephthalate, polypropylene terephthalate, polyvinyl chloride, propylene, polyethylene or mixtures thereof, and wherein the film is a film of a material selected from the group consisting of polyethylene terephthalate, polycarbonate, polyethylene, polypropylene, polyvinyl chloride and polystyrene.*

*75. The hygiene article as claimed in claim 72, wherein the hygiene article is in the form of a panty diaper, a diaper, an incontinence product, a panty liner, or a sanitary towel.*

*76. The hygiene article as claimed in claim 45, wherein the first fiber material is laminated to the film by the hot melt adhesive.*

*77. The hygiene article as claimed in claim 76, first the hot melt adhesive is disposed between the first fiber material and the film in an amount in the range of from 1 to 6 g/m$^2$.*

*78. The hygiene article as claimed in claim 76, wherein the first fiber material is selected from the group consisting of cotton, wool, silk, cellulose, linen, polyamide, polyester, polyethylene terephthalate, polypropylene terephthalate, polyvinyl chloride, propylene, polyethylene or mixtures thereof, and wherein the film is a film of a material selected from the group consisting of polyethylene terephthalate, polycarbonate, polyethylene, polypropylene, polyvinyl chloride and polystyrene.*

*79. The hygiene article as claimed in claim 76, wherein the hygiene article is in the form of a panty diaper, a diaper, an incontinence product, a panty liner, or a sanitary towel.*

*80. The hygiene article as claimed in claim 76, wherein the at least one polyolefin of the hot melt adhesive has a glass transition temperature $T_g$ of not more than −10° C. and a melt flow index MFI of greater than 30 g/10 min, measured in accordance with ISO 1133 at a temperature of 190° C. and under a load of 2.16 kg.*

*81. The hygiene article as claimed in claim 80, wherein the hot melt adhesive further comprises at least one tackifier resin in an amount, based on the total weight of the hot melt adhesive, in the range from 10 to 50% by weight, the at least one tackifier resin being at least one aliphatic, cycloaliphatic or aromatic hydrocarbon resin.*

*82. The hygiene article as claimed in claim 81, wherein the hot melt adhesive is disposed between the first fiber material and the film in an amount in the range of from 1 to 6 g/m$^2$.*

*83. The hygiene article as claimed in claim 82, wherein the first fiber material is selected from the group consisting of cotton, wool, silk, cellulose, linen, polyamide, polyester, polyethylene terephthalate, polypropylene terephthalate, polyvinyl chloride, propylene, polyethylene or mixtures thereof, and wherein the film is a film of a material selected from the group consisting of polyethylene terephthalate, polycarbonate, polyethylene, polypropylene, polyvinyl chloride and polystyrene.*

*84. A method for making the hygiene article as claimed in claim 25, the method comprising laminating the first fiber material to the film by disposing the hot melt adhesive between and in contact with the first fiber material and the film.*

*85. The method as claimed in claim 84, wherein the hot melt adhesive is disposed between the first fiber material and the film in an amount in the range of from 1 to 6 g/m$^2$.*

*86. A method for making the hygiene article as claimed in claim 35, the method comprising laminating the first fiber material to the film by disposing the hot melt adhesive between and in contact with the first fiber material and the film.*

*87. A method for making the hygiene article as claimed in claim 36, the method comprising laminating the first fiber material to the film by disposing the hot melt adhesive between and in contact with the first fiber material and the film.*

*88. A method for making the hygiene article as claimed in claim 49, the method comprising laminating the first fiber material to the film by disposing the hot melt adhesive between and in contact with the first fiber material and the film.*

*89. The hygiene article, panty diaper, diaper, incontinence product, panty liner or sanitary towel as claimed in claim 12, wherein the at least one polyolefin is a homopolymer of propylene or a copolymer of propylene and ethylene.*

*90. The hygiene article, panty diaper, diaper, incontinence product, panty liner or sanitary towel as claimed in claim 89, wherein the at least one polyolefin is a copolymer of propylene with from 0.1-30% by weight ethylene.*

*91. The hygiene article, panty diaper, diaper, incontinence product, panty liner or sanitary towel as claimed in claim 89, wherein the at least one polyolefin is a homopolymer of propylene.*

*92. The hygiene article as claimed in claim 25, wherein the at least one polyolefin is a homopolymer of propylene or a copolymer of propylene and ethylene.*

*93. The hygiene article as claimed in claim 92, wherein the at least one polyolefin is a copolymer of propylene with from 0.1-30% by weight ethylene.*

*94. The hygiene article as claimed in claim 92, wherein the at least one polyolefin is a homopolymer of propylene.*

* * * * *